United States Patent [19]
Alford et al.

[11] Patent Number: 5,133,220
[45] Date of Patent: Jul. 28, 1992

[54] ROTOR BORE INSPECTION SYSTEM

[75] Inventors: James W. Alford; Mark W. Fischer, both of Pittsburgh; Patricia A. Bosco, New Kensington; Alan A. Marfin, Pittsburgh; Vincent Berryman, Jr., Mars; Paul Guenther, Murrysville, all of Pa.; William B. Lutz, Ridgeland, Miss.; Wilbert B. Rethage, Apollo, Pa.

[73] Assignee: Westinghouse Electric Corp., Pittsburgh, Pa.

[21] Appl. No.: 385,865

[22] Filed: Jul. 26, 1989

[51] Int. Cl.$^5$ .............................. G01M 19/00
[52] U.S. Cl. .................... 73/866.5; 73/865.9
[58] Field of Search ............... 73/866.5, 865.8, 865.9, 73/623; 324/219, 220, 221; 356/378; 378/59, 60

[56] References Cited

U.S. PATENT DOCUMENTS

| | | | |
|---|---|---|---|
| 3,906,006 | 6/1976 | Smith | 73/622 |
| 4,073,859 | 2/1978 | Baumgartner et al. | 264/322 |
| 4,131,018 | 12/1978 | Müller et al. | 73/623 X |
| 4,481,814 | 11/1984 | Wentzell | 73/866.5 |
| 4,663,727 | 5/1987 | Saporito et al. | 73/623 X |
| 4,699,008 | 10/1987 | Feree et al. | 73/623 |
| 4,710,710 | 12/1987 | Flora et al. | 73/866.5 X |
| 4,757,716 | 7/1988 | Nottingham et al. | 73/623 |
| 4,856,337 | 8/1989 | Metala et al. | 73/623 X |

FOREIGN PATENT DOCUMENTS

| | | | |
|---|---|---|---|
| 2434467 | 2/1976 | Fed. Rep. of Germany | 73/623 |
| 862561 | 3/1961 | United Kingdom | 73/623 |

Primary Examiner—Tom Noland
Attorney, Agent, or Firm—M. G. Panian

[57] ABSTRACT

Apparatus for examining an elongated cylindrical body having an axial bore, such a rotor shaft, which apparatus includes an energy transducer which is supported by a drive rod to be advanced within the bore while obtaining readings indicative of the physical condition of the body, a drive unit supporting the rod, and a fixture for supporting the drive unit in order to center the drive rod within the bore, the fixture being supported by the body and including a mechanism for adjusting the fixture in order to establish the desired axial alignment of the drive rod. The fixture is provided with an arrangement for supporting a calibration block which is used for calibration of the apparatus, the arrangement being adjustable relative to the fixture to bring the calibration block into a desired position relative to the transducer when the drive unit is mounted on the fixture. The drive unit is rotated and advanced axially by DC permanent magnet motors and at least the motor which effects rotation of the drive rod is controlled by position and velocity error signals derived with the aid of a pulse encoder connected to rotate with the motor. A starting angular reference position of the body is determined with the aid of a further fixture which provides a flat reference surface having a defined orientation relative to a reference point on the body.

15 Claims, 5 Drawing Sheets

ROTOR BORE INSPECTION SYSTEM

CROSS REFERENCE TO RELATED APPLICATION

The subject matter of this application is related to that disclosed in U.S. patent application Ser. No. 07/079,860, filed Jul. 30, 1987, and now U.S. Pat. No. 4,856,337 and entitled APPARATUS AND METHOD FOR PROVIDING A COMBINED ULTRASONIC AND EDDY CURRENT INSPECTION OF A TUBE.

BACKGROUND OF THE INVENTION

The present invention is directed to an inspection system for ultrasonically inspecting a bore in an elongated shaft, such as the shaft of a turbine or generator rotor.

The rotor shafts of large machines, which are commonly provided with an axial bore, must be subjected to careful inspection, both at the time of manufacture and periodically after they have been placed into use in order to detect flaws which may occur during manufacture or may appear after a certain period of use and which could lead to premature, and possibly catastrophic, failure.

A variety of systems have been proposed and developed for performing various tests, each designed to detect a particular type of flaw. Systems of this type include those which effect ultrasonic inspections and eddy current inspections. Inspections of these types require the displacement of a transducer assembly through the bore, along the rotor axis, together with rotation of the assembly about that axis.

Such systems are described, for example, in U.S. Pat. Nos. 3,960,006, 4,699,008 and 4,757,716.

While the systems disclosed in these patents are capable of producing useful results, they have certain shortcomings. Thus, for example, known systems are not capable of rotating a transducer at a sufficiently constant velocity to permit optimum reading accuracy to be achieved. In addition, the known procedures for calibrating such systems, which must be performed before measurements are taken, are time consuming and can easily introduce certain inaccuracies into the measurement results. Further, in the known systems, proper positioning of the inspection system is a difficult and time consuming operation.

SUMMARY OF THE INVENTION

It is a primary object of the present invention to provide a novel rotor bore examination apparatus which alleviates these shortcomings and drawbacks.

One specific object of the invention is to provide a system which achieves improved control of the transducer head position during a measurement operation.

Yet another object of the invention is to facilitate and expedite calibration of the system prior to a measurement operation.

Still another object of the invention is to provide a more flexible and precise control of the transducer movements during a measurement operation.

Yet another object of the invention is to provide a system which is readily adaptable to a wide variety of rotor sizes.

The above and other objects are achieved, according to the present invention, in apparatus for examining an elongated cylindrical body having an axial bore, the apparatus including a head assembly carrying at least one energy transducer for monitoring a characteristic of the body, a drive rod supporting the head assembly, and a drive unit disposed outside the body and supporting the rod for moving the head assembly in translation along the bore axis and in rotation about the bore axis, by the provision of a device for supporting the drive unit to position the axis of the drive rod along the axis of the bore, the device comprising: first means for supporting the device from the body so that the first means have a fixed position relative to the body, and so that the device has a defined position relative to a vertical plane containing the bore axis; second means defining a support surface for the drive unit; and a mechanism coupled between the first and second means for displacing the second means vertically relative to the first means for bringing the second means to a defined position relative to a horizontal plane containing the bore axis.

Objects according to the invention are further achieved, when the apparatus is to be calibrated by bringing the transducer into operative association with a calibration member while the calibration member is in a defined position relative to the transducer, by the provision of a calibration member support unit mounted on the second means for supporting the calibration member at a location in proximity to the drive unit and for moving the calibration member relative to the second means to the defined position relative to the transducer.

In further accordance with the invention, the drive unit is provided with means for rotating the drive rod, comprising: a DC permanent magnet motor having a shaft coupled to rotate the drive rod at a speed proportional to the DC operating power supplied to the motor; electrically controllable means connected for supplying DC operating power to the motor; means for supplying control signals representative of the desired angular position and angular speed of the motor shaft; and feedback means connected for deriving feedback signals representative of the actual angular position and angular speed of the motor shaft; wherein the means for supplying DC operating power are connected to receive the control signals and the feedback signals and are operative for adjusting the power supplied to the motor in a direction to eliminate differences between the desired and actual position values and speed values.

In further accordance with the invention, the means for supplying DC operating power to the motor comprise: signal processing means for producing a direct analog signal representative of the DC operating power to be supplied to the motor: signal amplifier means having an electrically controllable variable gain, the signal amplifier means having an input connected to receive the direct analog signal produced by the signal processing means and a signal output; power amplifier means connected to the signal output of the signal amplifier means for supplying DC operating power to the motor; means forming a resistance in series between the power amplifier means and the motor; and means connected for controlling the gain of the signal amplifier means in a manner to maintain the current through the resistance below a selected value.

DESCRIPTION OF THE PREFERRED EMBODIMENTS

Figure 1:
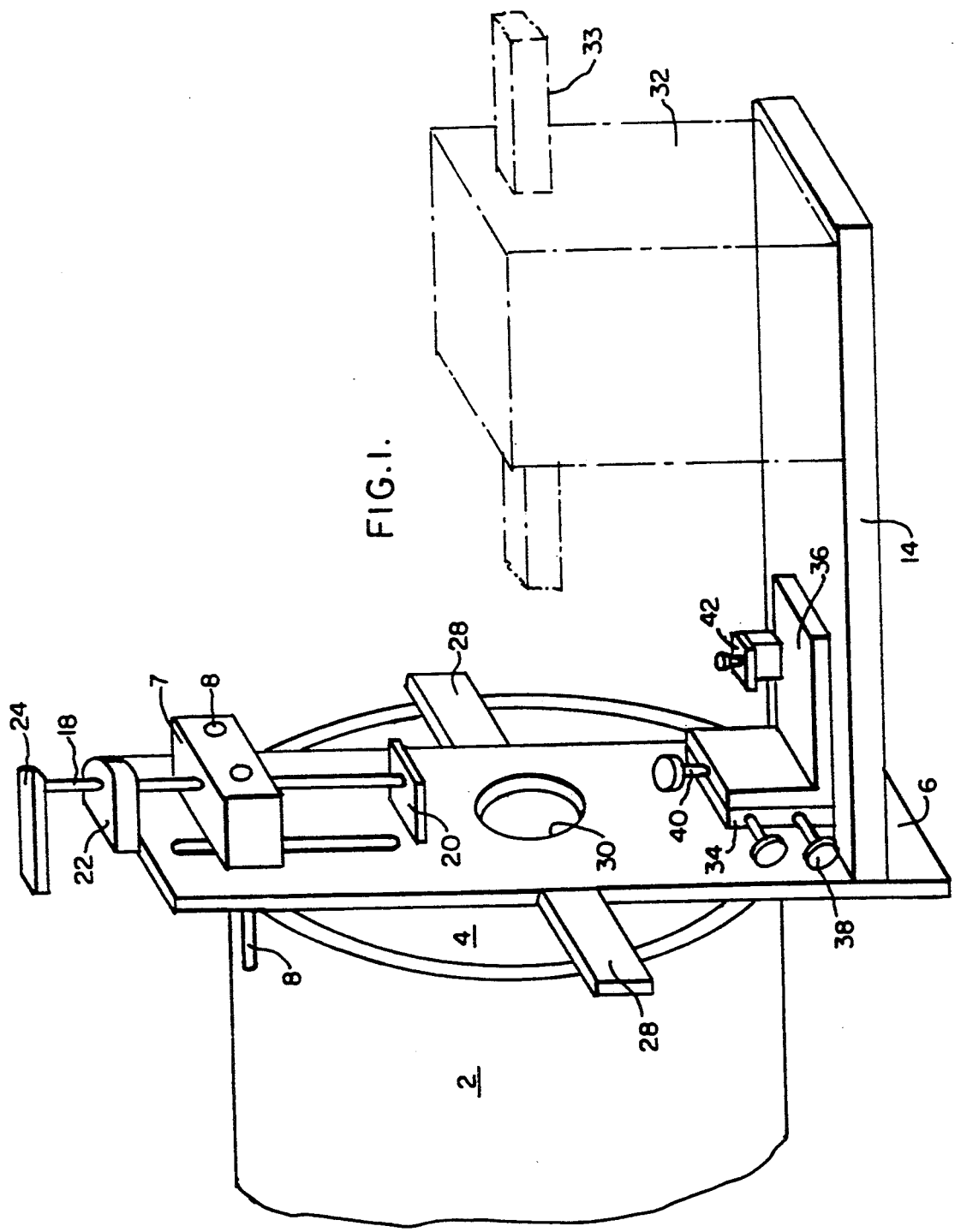
FIG. 1 is a perspective view of a support structure according to the present invention.

FIG. 1 illustrates an embodiment of a drive box support structure according to the invention mounted on one end of a rotor shaft 2 having a coaxial bore 4 which is to be examined. The support structure includes a vertical plate 6 provided, near its top, with a block 7 carrying two pins 8 disposed symmetrically with respect to the vertical center plane of the structure and provided to rest upon the outer cylindrical surface of shaft 2 in order to support the structure so that its vertical center plane is coincident with the axis of shaft 2. Since pins 8 are both at the same height and are disposed symmetrically to the vertical center plane of the structure, they will effect a nearly automatic horizontal centering of the structure. If it should prove difficult to achieve such centering under visual observation, plate 6 could be provided with a leveling device which will indicate when pins 8 are properly located relative to shaft 2, i.e. when the upper surface of plate 8 is perfectly horizontal, the structure will be properly positioned horizontally.

Plate 6 forms a rigid unit with a horizontal platform 14 and this unit is vertically movable relative to block 7 by means of a screw mechanism which includes a threaded shaft 18 which engages a threaded passage in block 7. Shaft 18 is held in place relative to plate 6 by bearing blocks 20 and 22 which permit rotation of shaft 18 while preventing vertical movement of shaft 18 relative to plate 6. Shaft 18 may be rotated manually by a crank handle 24 to raise and lower plate 6 and platform 14 relative to block 7 and pins 8.

Plate 6 is further provided with horizontal braces 28 for holding plate 6 in contact with the end of shaft 2. In addition, diagonal braces (not shown) may be fastened between plate 6 and platform 14.

Shaft 2 may be provided with an adapter ring having the cross section as shaft 2, or at least the same internal diameter as bore 4, against which plate 6 would bear.

Platform 14 supports the drive box 32 for the examination system and plate 6 is provided with a large central opening 30 for passage of a drive rod 33 supported by box 32 and carrying the transducer assembly of the inspection system. Opening 30 is at the same level as braces 28.

Plate 6 additionally carries a calibration block support unit composed of a first plate 34 which is held in a horizontal groove in plate 6 and an angle member 36 which is held in a vertical groove in plate 34. Plate 34 and member 36 may be displaced horizontally relative to plate 6 by a conventional mechanism including a lead screw 38 and member 36 may be displaced vertically relative to plate 34 by a similar mechanism including a lead screw 40. Member 36 may be provided with one or more clamps 42 for securing a calibration block in place.

After the structure shown in FIG. 1 has been placed on shaft 2 in the manner illustrated, crank handle 24 is rotated to vertically align opening 30 with the center line of bore 4. Establishment of the desired alignment can be monitored visually or by means of suitable gauges which will indicate that the proper position has been achieved. Then, if necessary, plate 6 and/or braces 28 may be clamped to shaft 2 in order to assure that the support structure will remain in the desired position during the subsequent examination procedure.

Then, with the examination apparatus, which includes drive box 32, drive rod 33 and a transducer support by rod 33, mounted in place on platform 14, a standard calibration block is mounted on angle member 36 and, if necessary, is clamped in place. One conventional type of calibration block is a metal body having an opening of the same diameter as the bore to be examined and provided, in the surface corresponding to the bore surface, with, for example, holes having selected depths. When a transducer head is caused to scan the surface, its output signal can be compared with a previously derived calibration signal to indicate whether the transducer head and its associated circuitry are correctly calibrated.

The calibration block support unit 34, 36 provided according to the present invention enables a calibration block to be brought into a position in which it is aligned with the bore 4 to be examined so that the calibration operation can be performed with the examination system already in position to perform a bore examination operation. This means that after the calibration procedure has been completed, the calibration block can be removed, without changing the position of the examination system relative to the bore. Therefore, a calibration operation will be performed with the same transducer contact pressure and alignment as the subsequent examination procedure and one source of reading errors will be eliminated due to the fact that the examination system need not be repositioned subsequent to completion of the calibration procedure. Moreover, this arrangement enables the calibration procedure to be carried out under the same scanning conditions as those which will be employed during the examination procedure.

Since the calibration block support structure is adjustable horizontally and vertically, it can be adapted to a range of rotor bore sizes and to a range of calibration block configurations.

During an examination procedure, a transducer/head assembly which is dimensioned to fit within the rotor bore is supported by drive rod 33. In order to maintain drive rod 33 in alignment with the bore axis, bushings may be secured to the drive rod at positions spaced along its length, which bushings include members which rest upon, and slide relative to, the surface of bore 4. Bushings of this type are known in the art.

Figure 2:
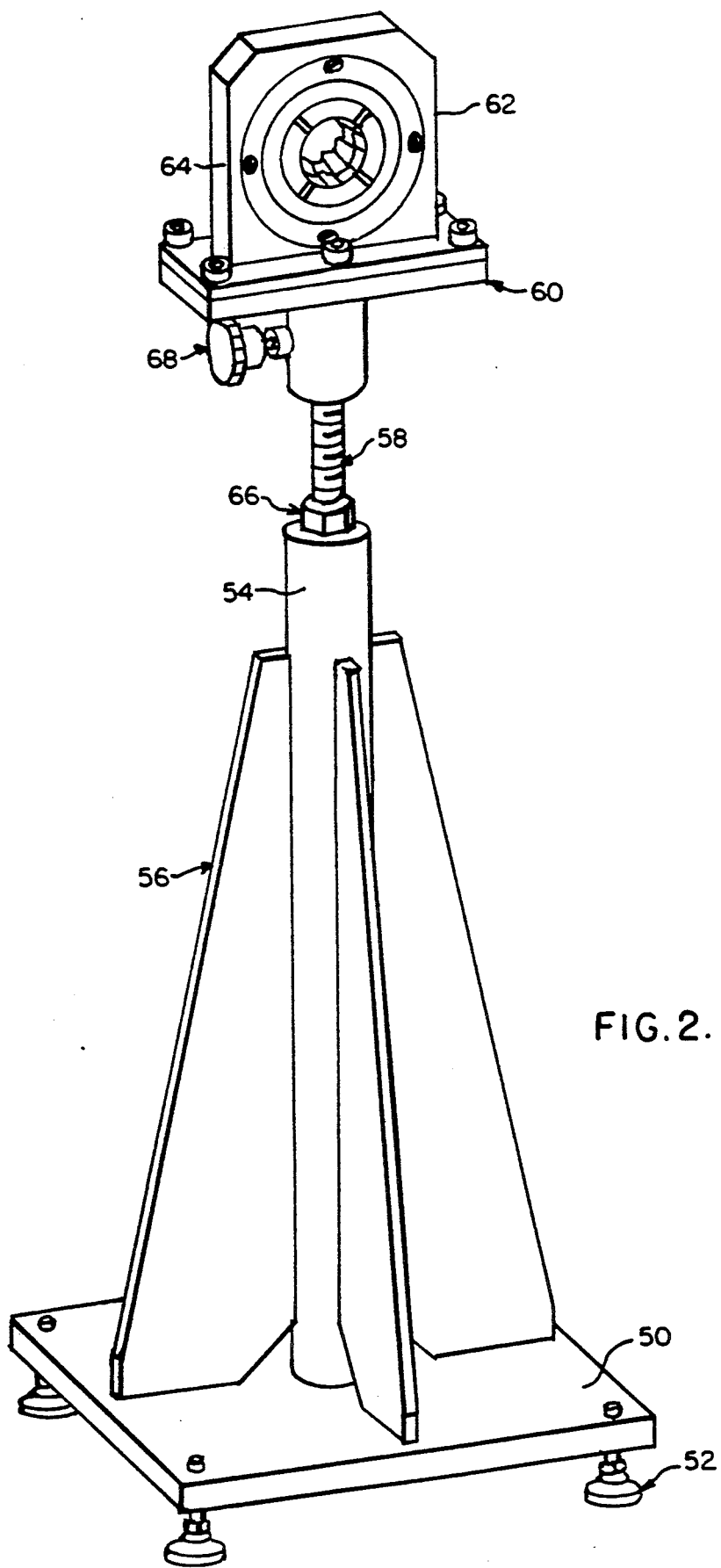
FIG. 2 is a perspective view of a drive rod support stand according to the invention.

To provide additional support for drive rod 33, the portion thereof which extends from the rear of drive box 32 may, according to the invention, be supported by a support stand, one embodiment of which is illustrated in FIG. 2. This stand would be disposed to the right of the arrangement shown in FIG. 1.

The support stand shown in FIG. 2 includes a base 50 provided with a plurality of leveling pads 52 and carrying a vertical support tube 54 stabilized by vertical support plates 56. Within tube 54 there is a vertical support rod 58 carrying a support plate 60 which, in turn, supports a bearing housing 62 containing a rotatably mounted bushing 64 for receiving and supporting the rear end of drive rod 33 while permitting rotation and axial displacement of rod 33. The height of the support stand may be adjusted by means of a nut 66 which rests on the top of tube 54 and engages threads on the outer surface of rod 58. Bushing 64 can be locked in a selected angular position by a clamping screw having a locking knob 68.

If required, a plurality of the support stands shown in FIG. 2 can be arranged in a line behind drive box 32 of FIG. 1.

In order for the readings produced during an examination procedure of the type contemplated by the present invention to be accurately correlated with physical locations within bore 4, it is necessary, prior to the start of an examination procedure, to determine the starting angular position of a reference point on the shaft relative to a reference orientation of the transducer/head assembly. Commonly, a rotor shaft, or an adapter coupled to one end of the shaft, will include at least one marking, frequently in the form of a hole, which can serve as a zero degree reference for the examination system. Thus, if the inclination of a line between such reference marking and the axis of the shaft is known, then the information produced during an examination procedure can be correctly correlated to physical locations within the bore.

Presently, various techniques are used to obtain such reference angle, but these techniques are subject to various sources of error which will increase the difficulty of achieving an accurate correlation.

Figure 3:
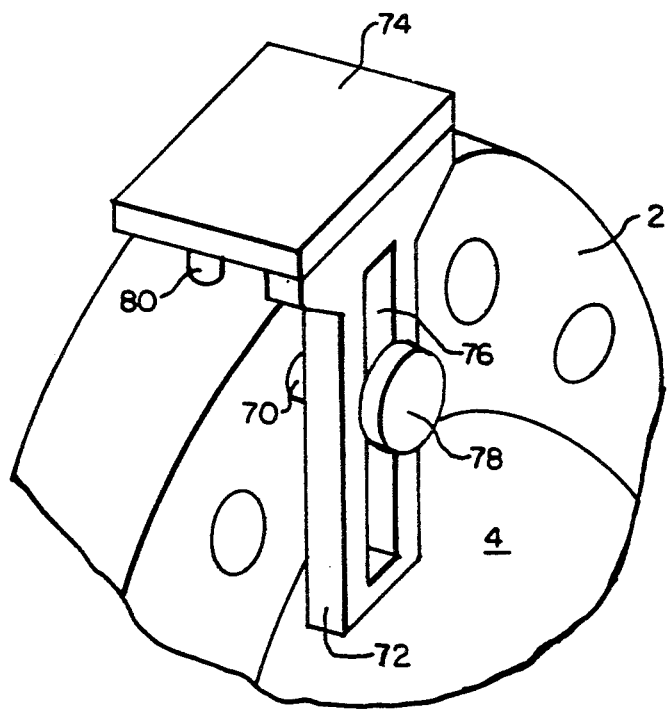
FIG. 3 is a perspective view of a reference angle measurement fixture according to the present invention.

According to the present invention, a more precise determination of the reference angle is obtained by the use of a special fixture having a reference surface which will be accurately oriented relative to the circumference of the rotor shaft, or of an adapter coupled to the shaft, at the location of such reference mark or hole. A preferred embodiment of such a fixture is illustrated in FIG. 3. It should be noted, however, that the precise configuration of the fixture can be varied, depending on the nature of the markings with which it is to be used.

The embodiment shown in FIG. 3 is constructed for use with a rotor shaft 2, or an adapter coupled thereto, provided with at least one hole 70 which can serve as a reference mark. The fixture according to the present invention is in the form of an angle member having a leg 72 arranged to extend in a radial direction relative to rotor 2 and a platform 74 extending perpendicular to leg 72. Leg 72 is provided with an elongated slot 76 containing a pin having a head 78. The pin is dimensioned to fit securely in hole 70 in a manner such that platform 74 will be oriented tangentially to a point on the cylindrical surface of shaft 2, or an adapter connected thereto, which is radially aligned with the center of hole 70. To assist this operation, platform 74 may be provided with two spherical positioning balls 80, only one of which is visible in FIG. 3, arranged so that when the pin in slot 76 is inserted into hole 70 and both feet 80 rest upon the circumferential surface of shaft 2, platform 74 is correctly oriented.

Then, any suitable type of angle measuring device, such as a commercially available digital protractor, can be placed upon platform 74, and a reference angle reading can be taken therefrom. This reading will then be set into the digital system that will be employed to control the movement of the transducer/head assembly and to coordinate the readings obtained thereby with locations along the surface of rotor bore 4.

When a rotor bore examination is to be performed, the transducer/head assembly carried by the support rod is rotated through an angle at least slightly greater than 360° about the bore axis a plural of times and is advanced in steps along the bore axis. According to one conventional procedure, the transducer/head assembly is rotated in alternatingly opposite directions in order to avoid breakage of the conductors extending between the transducer/head assembly and the devices for supplying excitation signals to, and collecting received signals from, the transducer/head assembly.

According to the present invention, the transducer/head assembly is rotated in a continuing manner while the angular position of the assembly is controlled with a high degree of accuracy sufficient to allow accurate measurements to be taken while the assembly rotates continuously during each revolution.

In the operation of a system according to the invention, it is also possible to effect incremental rotation of the transducer/head assembly, particularly after a flaw has been detected. In this situation, continuous rotation is halted and the assembly is rotated, possibly under manual control, or under computer control, to bring it to the angular position at which the flaw indication has a peak value. The use of a DC permanent magnet servomotor which operates in response to a continuous signal enables the position of the head to be set with a high degree of precision. The head position then provides an accurate indication of the location of the flaw.

Briefly stated, this improvement is achieved by the use of a DC permanent magnet servo motor which receives continuous drive power, and by obtaining an accurate indication of the rotational movement of the motor, deriving from this indication both position information and velocity information, and utilizing this information in a feedback path to effect accurate control of the motor rotation. It has been found that when the motor is controlled on the basis of both position and velocity indications, the angular position of the transducer can be maintained sufficiently close to a desired angular position to allow the transducer to rotate continuously while ultrasonic readings are taken.

Stated in other terms, if the data collecting system, which is generally a digital computer controlled system, can assume that the transducer is at defined angular positions at specified points in time, then ultrasonic readings taken while the transducer head rotates in a continuous manner, even at a relatively high speed, can be accurately correlated with the portion of the rotor shaft which produces those readings.

Figure 4:
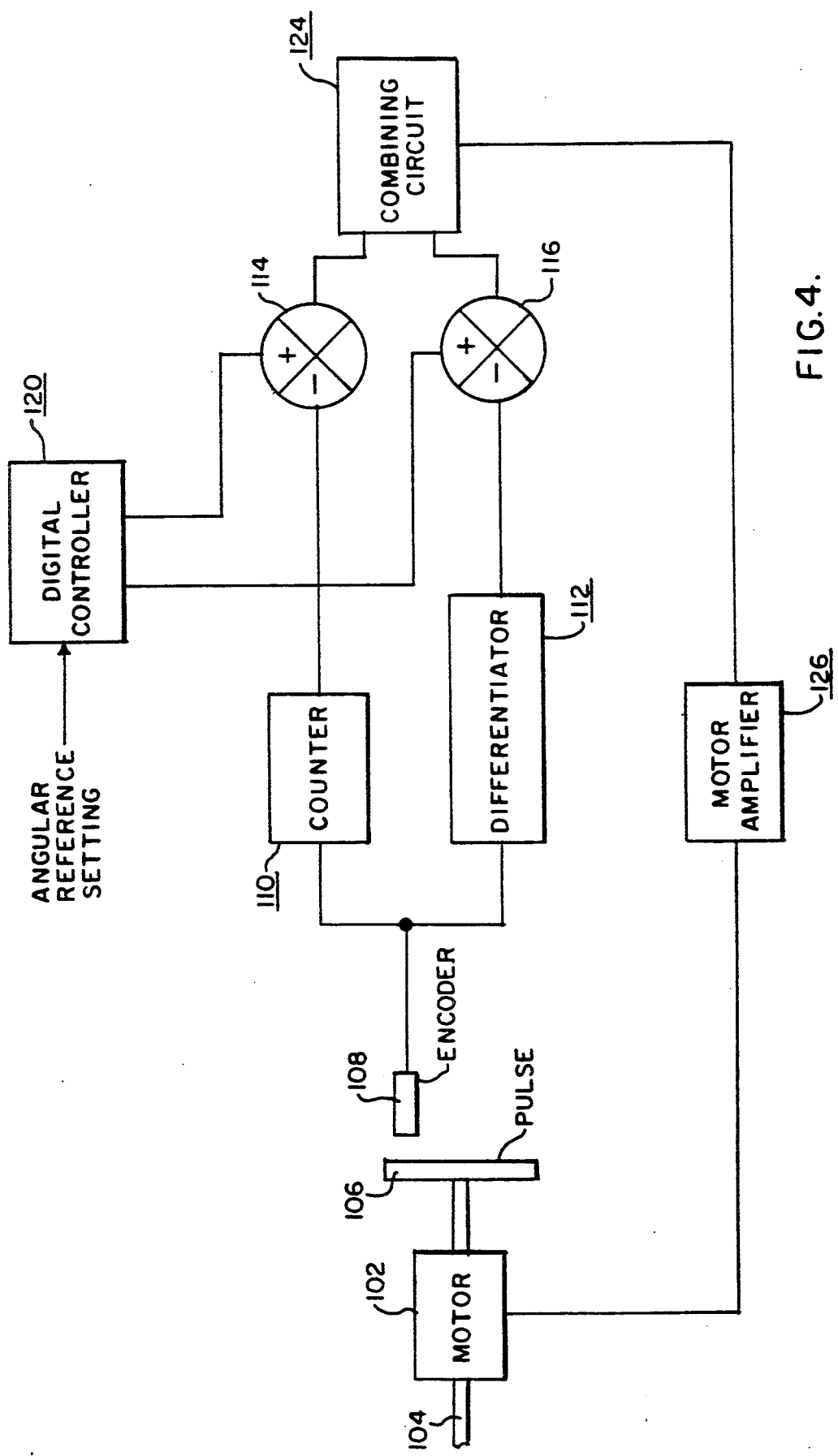
FIG. 4 is a block diagram of a motor control system according to the present invention.

A feedback system for controlling the operation of a DC permanent magnet servo motor is illustrated in FIG. 4. The drive rod 33 carrying a transducer/head assembly for an ultrasonic examination system is rotated by DC permanent magnet servo motor 102 having an output shaft 104 coupled to the drive rod. This coupling may be direct or via a gear train, depending on the speed and power characteristics of motor 102 and the speed at which the contemplated by the present invention, accurate indications can be obtained with a head rotation rate such that each transducer traverses the bore surface at a maximum speed of 1.25 cm/sec.

Shaft 104 is additionally coupled to a pulse encoder 106 which is a disk provided with a circular array of apertures arranged to intersect a light beam. Light passing through these apertures strikes a light receiver 108 which produces an electrical output in the form of a train of pulses each representative of a predetermined increment of rotation of shaft 104 and having a pulse rate representative of the speed of shaft rotation. This pulse train is supplied to the input of a counter 110 and to the input of a differentiator 112.

The output of counter 110 is a count signal having a magnitude indicative of the extent of angular movement of motor shaft 104 from a reference position, while the output signal from the differentiator 112 has a magnitude representative of the present angular speed of motor shaft 104. Each of these signals is supplied to the subtracting input of a respective difference former 114, 116 the adder inputs of which are connected to receive signals from a digital controller 120.

Digital controller 120 is controlled by a digital data processing system to supply programmed signals representative of the desired instantaneous position and velocity of motor shaft 104. In view of the flexibility afforded by digital processing systems, these signals can have any desired waveform. In the simplest case, the desired position signal would be in the form of a linear ramp function and the desired velocity signal would have a constant amplitude.

The outputs of difference formers 114 and 116, which constitute position and velocity error signals, respectively, are supplied to a suitable combining circuit 124 which combines the signals according to a predetermined weighting function in order to produce a suitable motor control signal. The weighting function will be determined, as is well known in the art, on the basis of the characteristics of motor 102 in achieve an optimum position control. The error signal produced by circuit 124 is supplied to a motor amplifier 126 which preferably supplies motor 102 with operating power having a linear relation to the motor control signal. Preferably, amplifier 126 is a high gain device which will drive motor 102 in a manner to maintain a small, substantially constant difference between the actual motor position and the desired motor position, the difference being sufficiently small to not adversely effect the accuracy of the resulting ultrasonic signal readings.

It would further be possible, in the spirit of the present invention, to derive acceleration signals by differentiating the velocity signal from differentiator 112, compare the resulting acceleration indication with a desired acceleration value provided by controller 120, and supply the resulting acceleration difference signal to combining circuit 24, in which it would be employed, with proper weighting, in the production of the signal supplied to motor amplifier 126.

The circuit components illustrated in FIG. 4 could be digital devices, in which case the output signal from combining circuit 124 would be subjected to a digital-analog conversion before delivery to amplifier 126. Alternatively, the output signals from counter 110, differentiator 112 and controller 120 could all be subjected to digital-analog conversion, in which case difference formers 114 and 116 and combining circuit 124 would be analog devices.

Digital controller 120 receives, in addition to position and velocity control information, a signal indicating the angular reference setting defining the starting angular position between the transducer/head assembly and the rotor shaft. This setting can be introduced manually prior to the start of an examination procedure, based on a reading taken with the aid of the fixture shown in FIG. 3.

According to a further feature of the invention, motor amplifier 126 is. constructed as a linear type motor amplifier in that it receives a continuous analog input signal the amplitude of which determines the level of power supplied to the motor. The advantage of such an amplifier is that the signals associated therewith do not include high frequency components which would be a source of electrical noise that would interfere with the readings provided by the ultrasonic transducer. Such high frequency noise is produced, for example, in amplifiers which are controlled by a pulse width modulated signal.

When such a linear amplifier is employed to drive a motor, it is desirable to employ current limiting in order to protect the motor and the mechanical system which it drives if that system should encounter, for example, an obstruction which will increase the mechanical load on the motor, and hence tend to increase the current which it draws. It is known to effect current limiting by a circuit including a sense resistor which monitors the current being supplied to the motor and an internal transistor which is rendered conductive in order to dissipate excess current whenever the current level goes above a selected value. However, with this arrangement, the excess current must be dissipated by the amplifier itself, and this will result in undesired heating of the amplifier.

The present invention provides a novel current limiting system which effectively protects the motor without requiring the amplifier to perform such current dissipating action.

Figure 5:
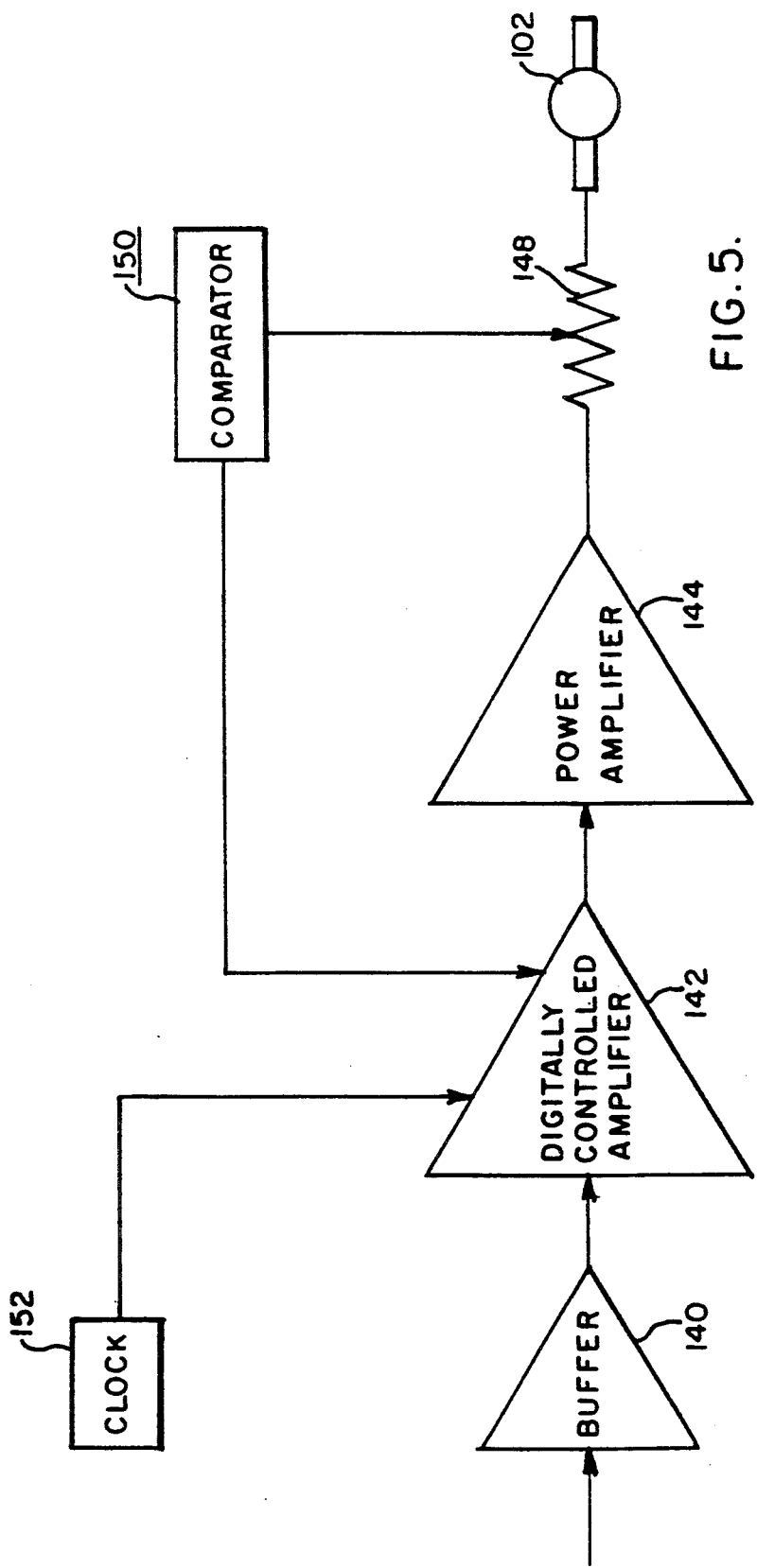
FIG. 5 is a schematic diagram of a motor power amplifier according to the present invention.

One preferred embodiment of a motor amplifier according to the present invention is illustrated in FIG. 5. This circuit includes a buffer amplifier 140 connected to receive the analog signal supplied by combining circuit 124 of FIG. 4, a digitally controlled amplifier 142 and a power amplifier 144 arranged in cascade.

In the operation of the system shown in FIG. 5, a low level signal from combining circuit 124 of FIG. 4 is supplied to the input of buffer amplifier 140 and is subjected to amplification in amplifier 142. The amplified signal from amplifier 142 is supplied to power amplifier 144 whose output represents the power level required to drive motor 102 at the speed indicated by the signal supplied by circuit 124. Amplifier 142 supplies a relatively low level signal to amplifier 144.

Connected in series between the output of amplifier 144 and motor 102 is a current sense resistor 148 from which is derived a signal representative of the level of current flow therethrough. This signal is supplied to one input of a comparator 150 which additionally receives an input signal, produced for example by the digital control system, representative of a preset current level.

The output signal from comparator 150 is supplied to amplifier 142 to control a digitally adjustable potentiometer forming part of amplifier 142. Such amplifiers are well known in the art.

Amplifier 142 further receives a clock signal from a clock 152, the pulse rate of the clock signal determining the frequency with which the gain of amplifier 142 is varied under control of the signal supplied by comparator 150.

The output signal from comparator 150 acts to vary the gain of amplifier 142 in a manner to prevent the current supplied to motor 102 from exceeding a preset level. Thus, effective current limiting is provided without creating the need to dissipate excess current.

While a reduction in the current level will effect the speed of rotation of the motor, it will have the more significant effect of protecting the motor and the transducer which it drives from damage since current limiting will normally be performed only if the transducer encounters an obstruction or if some other abnormal condition should occur.

A system similar to that shown in FIGS. 4 and 5 will additionally be employed for controlling the motor which effects axial displacement of the transducer/head assembly. The only change required is in the configuration, or waveform, of the control signal, or signals, supplied to difference formers 114 and 116. In addition, since the axial displacement of the transducer/head assembly is intermittent, or stepped, the speed of the motor producing axial displacement need not be controlled with the same procedure as that of the motor controlling rotational movement of the transducer/head assembly. Thus, it would be possible, for controlling the axial displacement motor, to eliminate the velocity control channel of the circuit shown in FIG. 4.

If only position feedback control is employed, this control can be effected in a manner to produce rapid movement of the transducer from its present axial position to the next axial position. This can be achieved, for example, by supplying control signals to difference former 114 from controller 120 which have a form such as to impart a constant acceleration to the motor until a desired velocity value, or a desired amount of displacement, has been achieved, followed by a signal which cause the motor to operate at a constant speed until the transducer/head assembly reaches a position a fixed distance from the desired final position, after which a signal producing a constant deceleration is supplied to the motor to bring it to the desired final position.

Figure 6A:
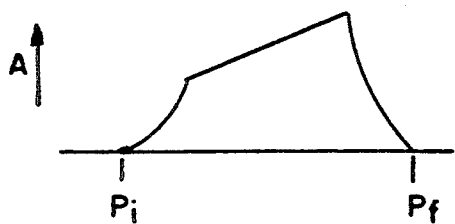
FIGS. 6a and 6b are signal waveform diagrams illustrating the control of an axial drive motor according to the present invention.
Figure 6B:
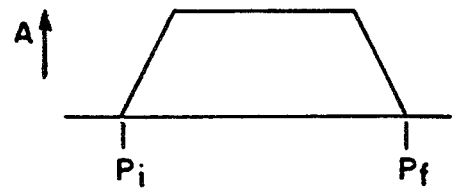

The analog values represented by the digital signals supplied to perform this operation are depicted in FIGS. 6a and 6b. FIG. 6a represents the analog value of the digital position signal that would be supplied by controller 120 to difference former 114 to control such axial displacement, while FIG. 6b illustrates the analog value of the corresponding velocity signal which could optionally be supplied to difference former 116.

As is shown in FIG. 6a, to effect axial displacement of a transducer, the signal supplied to difference former 114 initially varies in value according an ascending parabolic function, which corresponds to the production of a linear acceleration. After a time corresponding to a given amount of rotation of the shaft of the associated motor, the signal provided by controller 120 begins to vary according to a linear function, corresponding to a constant motor shaft velocity. At a subsequent point in time, the signal provided by controller 120 changes to a descending parabolic function which reaches a value of zero at a point corresponding to the desired final position of the transducer/head assembly.

If, in order to achieve, more precise control of this movement, a velocity signal is also provided by controller 120, it would have the form shown in FIG. 6b, including a linear ascending portion representing, as noted above, a linearly increasing velocity, followed by a level portion at which the velocity of the motor is maintained constant, and ending with a linearly descending portion which reaches a value of zero at a time corresponding to the desired final position.

In view of the feedback function performed by the circuit of FIG. 4, the motor effecting axial movement of the drive rod, and thus of the transducer/head assembly, will accurately follow the position and velocity values provided by controller 120.

The motor which effects axial displacement of the drive rod and the transducer/head assembly can be of the same type as that which produces rotation of the drive rod and the transducer/head assembly.

According to a preferred embodiment of the invention, the motion control system shown in FIG. 4 can incorporate a commercially available motion controller such as model DMC-420 marketed by Galil Motion Control of Palo Alto, Ca. This controller additionally includes an acceleration control channel which could be employed to control each of the motors used in the system according to the present invention.

Digital signals for triggering the production of ultrasonic pulses by the transducer/head assembly and for receiving, storing and analyzing the reflection signals received by that assembly can be derived according to techniques already known in the art based on the principles employed in connection with rotor bore examination procedures. The digital control system can be based on a host computer of the IBM/AT architecture controlled by programming which is either known or which can be derived, based on the descriptions presented herein, according to principles known in the art.

While the above description has been directed to an ultrasonic examination system, the invention could also be applied to other types of two-axis detection systems, eddy current detection systems, alone or in combination with an ultrasonic examination system for monitoring physical conditions other than flaws.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. In apparatus for examining an elongated cylindrical body having an axial bore, the apparatus including an energy transducer for monitoring a characteristic of the body, a drive rod supporting the transducer, and a drive unit disposed outside the body and supporting the rod for moving the transducer in translation along a longitudinal axis of the bore and in rotation about the bore axis and including means for rotating and axially advancing the drive rod, the improvement comprising a device for supporting the drive unit to position a longitudinal axis of the drive rod along the axis of the bore, said device comprising: first means for supporting said device from the body so that said first means have a fixed position relative to the body, and said device has a defined position relative to a vertical plane containing the bore axis; second means defining a support surface for the drive unit; and a mechanism coupled between said first and second means for displacing said second means vertically relative to said first means for bringing said second means to a defined position relative to a horizontal plane containing the bore axis said mechanism comprising a manually actuable screw.

2. Apparatus as defined in claim 1 wherein the body is a rotor shaft having a cylindrical outer surface and said first means comprise two horizontally spaced members arranged to rest upon the outer surface of the rotor shaft.

3. Apparatus as defined in claim 1 which is to be calibrated by bringing the transducer into operative association with a calibration member while the calibration member is in a defined position relative to the transducer, and further comprising calibration member support means mounted on said second means for supporting the calibration member at a location in proximity to the drive unit and for moving the calibration member relative to said second means to the defined position relative to the transducer.

4. Apparatus as defined in claim 1 further comprising a drive rod support member disposed for supporting the drive rod at a side of the drive unit remote from the body when the drive unit is disposed on said support surface.

5. The apparatus as defined in claim 1 wherein said means for rotating the drive rod comprises: a DC permanent magnet motor having a shaft coupled to rotate said drive rod at a speed proportional to the DC operating power supplied to said motor; electrically controllable means connected for supplying DC operating power to said motor; means for supplying control signals representative of the desired angular position and angular speed of said motor shaft; and feedback means connected for deriving feedback signals representative of the actual angular position and angular speed of said motor shaft; wherein said means for supplying DC operating power are connected to receive the control signals and the feedback signals and are operative for adjusting the power supplied to said motor in a direction to eliminate differences between the desired and actual position values and speed values.

6. Apparatus as defined in claim 5 wherein said means for supplying DC operating power to said motor comprise: signal processing means for producing a direct analog signal representative of the DC operating power to be supplied to said motor: signal amplifier means having an electrically controllable variable gain, said signal amplifier means having an input connected to receive the direct analog signal produced by said signal processing means and a signal output; power amplifier means connected to said signal output of said signal amplifier means for supplying DC operating power to said motor; means forming a resistance in series between said power amplifier means and said motor; and means connected for controlling the gain of said signal amplifier means in a manner to maintain the current through said resistance below a selected value.

7. Apparatus as defined in claim 6 wherein said means connected for controlling the gain of said signal amplifier means are connected to said means forming a resistance for sensing the current flowing between said power amplifier means and said motor.

8. Apparatus for examining a rotor shaft having a cylindrical outer surface and a bore having a longitudinal axis, the apparatus including an energy transducer for monitoring a characteristic of the rotor shaft, a drive rod supporting the transducer, and a drive unit disposed outside the bore and supporting the rod for moving the transducer in translation along the longitudinal axis of the bore and in rotation thereabout, a device for supporting the drive unit to position a longitudinal axis of the drive rod along the axis of the bore, said device comprising first means for supporting said device from the rotor shaft so that first means have a fixed position relative to the rotor shaft, and said device has a defined position relative to a vertical plane containing the longitudinal axis of the bore, second means defining a support surface for the drive unit, a mechanism coupled between said first and second means for displacing said second means vertically relative to said first means for bringing said second means to a defined position relative to a horizontal plane containing the longitudinal axis of the bore, means for bringing the transducer into operative association with a calibration member while the calibration member is in a defined position relative to the transducer, and calibration member support means mounted on said second means for supporting the calibration member at a location in proximity to the drive unit and for moving the calibration member relative to said second means to the defined position relative to the transducer.

9. Apparatus as defined in claim 8 wherein said mechanism comprises a manually actuable screw mechanism.

10. Apparatus as defined in claim 9 wherein said first means comprise two horizontally spaced member arranged to rest upon the outer surface of the rotor shaft.

11. Apparatus as defined in claim 10 further comprising a drive rod support member as disposed for supporting the drive rod at a side of the drive unit remote from the rotor shaft when the drive unit is disposed on said support surface.

12. The apparatus as defined in claim 11, wherein said drive unit includes means for rotating the drive rod, said means for rotating the drive rod comprising: a DC permanent magnet motor having a shaft coupled to rotate said drive rod at a speed proportional to the DC operating power supplied to said motor; electrically controllable means connected for supplying DC operating power to said motor; means for supplying control signals representative of the desired angular position and angular speed of said motor shaft; and feedback means connected for deriving feedback signals representative of the actual angular position and angular speed of said motor shaft; wherein said means for supplying DC operation power are connected to receive the control signals and the feedback signals and are operative for adjusting the power supplied to said motor in a direction to eliminate differences between the desired and actual position values and speed values.

13. Apparatus as defined in claim 12 wherein said means for supplying DC operating power to said motor comprise: signal processing means for producing a direct analog signal representative of the DC operating power to be supplied to said motor: signal amplifier means having an electrically controllable variable gain, said signal amplifier means having an input connected to receive the direct analog signal produced by said signal processing means and a signal output; power amplifier means connected to said signal output of said signal amplifier means for supplying DC operating power to said motor; means forming a resistance in series between said power amplifier means and said motor; and means connected for controlling the gain of said signal amplifier means in a manner to maintain the current through said resistance below a selected value.

14. Apparatus as defined in claim 13 wherein said means connected for controlling the gain of said signal amplifier means are connected to said means forming a resistance for sensing the current flowing between said power amplifier means and said motor.

15. In apparatus for examining a rotor shaft having an axial bore, the apparatus including an energy transducer for monitoring a characteristic of the rotor shaft, a drive rod supporting the transducer, and a drive unit disposed outside the rotor shaft and supporting the rod for moving the transducer in translation along the bore axis and in rotation about the bore axis, the improvement wherein said drive unit comprises means for rotating the drive rod, comprising:

a DC permanent magnet motor having a shaft coupled to rotate said drive rod at a speed proportional to the DC operating power supplied to said motor;

electrically controllable means for supplying DC operating power to said motor comprising signal processing means for producing a direct analog signal representative of the DC operating power to be supplied to said motor, signal amplifier means having an electrically controllable variable gain, said signal amplifier means having an input connected to receive the direct analog signal produced by said signal processing means and a signal output;

power amplifier means connected to said signal output of said signal amplifier means for supplying DC operating power to said motor;

means forming a resistance in series between said power amplifier means and said motor;

means connected for controlling the gain of said signal amplifier means in a manner to maintain the current through said resistance below a selected value;

means for supplying control signals representative of the desired angular position and angular speed of said motor shaft;

and feedback means connected for deriving feedback signals representative of the actual angular position and angular speed of said motor shaft, wherein said means for supplying DC operating power are connected to receive the control signals and the feedback signals and are operative for adjusting the power supplied to said motor in a direction to eliminate differences between the desired and actual position values and speed values.

* * * * *